United States Patent
Lee

(10) Patent No.: US 11,893,124 B2
(45) Date of Patent: *Feb. 6, 2024

(54) METHOD FOR BUILDING CLOUD-BASED MEDICAL IMAGE DATABASE FOR PROTECTION OF PATIENT INFORMATION AND READING MEDICAL IMAGE THEREFROM

(71) Applicant: IRM INC., Gyeonggi-do (KR)

(72) Inventor: Minhwa Lee, Seoul (KR)

(73) Assignee: IRM INC., Gyeonggi-do (KR)

( * ) Notice: Subject to any disclaimer, the term of this patent is extended or adjusted under 35 U.S.C. 154(b) by 114 days.

This patent is subject to a terminal disclaimer.

(21) Appl. No.: 17/714,210

(22) Filed: Apr. 6, 2022

(65) Prior Publication Data

US 2022/0229827 A1 Jul. 21, 2022

Related U.S. Application Data

(63) Continuation of application No. 15/771,204, filed as application No. PCT/KR2016/012077 on Oct. 26, 2016, now Pat. No. 11,327,943.

(30) Foreign Application Priority Data

Oct. 26, 2015 (KR) .......................... 10-2015-0148797

(51) Int. Cl.
*G16H 30/00* (2018.01)
*G06F 21/62* (2013.01)
(Continued)

(52) U.S. Cl.
CPC .............. *G06F 21/62* (2013.01); *G06F 16/23* (2019.01); *G06F 16/50* (2019.01);
(Continued)

(58) Field of Classification Search
CPC .......................... G16H 30/20; G06Q 50/22–24
See application file for complete search history.

(56) References Cited

U.S. PATENT DOCUMENTS 7,860,760 B2 * 12/2010 Smith ................ H01R 13/7175
705/26.81
9,152,816 B2 10/2015 Park et al.
(Continued)

FOREIGN PATENT DOCUMENTS

CN 106354994 A 1/2017
JP S63257873 A 10/1988
(Continued)

*Primary Examiner* — John A Pauls
(74) *Attorney, Agent, or Firm* — Studebaker & Brackett PC

(57) ABSTRACT

Provided is a method of building a cloud-based medical image database for protecting patient information and reading medical image therefrom, the method including: acquiring a medical image of a patient by using a medical apparatus; separating medical information data and patient information data from the medical image; encrypting the patient information data by using a block chain technique; separately transmitting the encrypted patient information data and the medical information data to the cloud-based medical image database, and storing the same in the cloud-based medical image database; decrypting the encrypted patient information data stored in the cloud-based medical image database by using a block chain technique; and performing diagnosis and consulting by reading the medical information data and the patient information data of the medical image according to a big data processing algorithm. Therefore, the method may protect patient's personal information and determine the cause and progress of a disease.

12 Claims, 2 Drawing Sheets

(51) Int. Cl.
  *G06F 16/23* (2019.01)
  *G06F 16/50* (2019.01)
  *G06F 21/64* (2013.01)
  *H04L 9/32* (2006.01)
  *H04L 9/08* (2006.01)
  *G16H 50/70* (2018.01)
  *G16H 30/40* (2018.01)
  *G06Q 10/10* (2023.01)
  *G16H 10/60* (2018.01)
  *H04L 9/06* (2006.01)
  *G16H 30/20* (2018.01)
  *G16H 50/20* (2018.01)
  *G06F 16/10* (2019.01)
  *H04L 9/00* (2022.01)

(52) U.S. Cl.
  CPC .......... *G06F 21/6245* (2013.01); *G06F 21/64* (2013.01); *G06Q 10/10* (2013.01); *G16H 10/60* (2018.01); *G16H 30/20* (2018.01); *G16H 30/40* (2018.01); *G16H 50/20* (2018.01); *G16H 50/70* (2018.01); *H04L 9/06* (2013.01); *H04L 9/0825* (2013.01); *H04L 9/3239* (2013.01); *G06F 16/10* (2019.01); *H04L 9/50* (2022.05); *H04L 2209/88* (2013.01)

(56) References Cited

U.S. PATENT DOCUMENTS

| | | | |
|---|---|---|---|
| 2002/0035485 A1 | 3/2002 | Mita et al. | |
| 2011/0110568 A1* | 5/2011 | Vesper | G06Q 10/10 382/128 |
| 2011/0125801 A1* | 5/2011 | DiRienzo | G06Q 30/06 707/791 |
| 2013/0006867 A1* | 1/2013 | Dove | H04L 9/083 707/827 |
| 2015/0332283 A1* | 11/2015 | Witchey | G16H 10/60 705/3 |
| 2015/0379510 A1* | 12/2015 | Smith | G06Q 20/3829 705/71 |
| 2017/0039330 A1* | 2/2017 | Tanner, Jr. | G06Q 20/065 |
| 2017/0091397 A1* | 3/2017 | Shah | H04L 63/20 |

FOREIGN PATENT DOCUMENTS

| | | |
|---|---|---|
| JP | 2008029419 A | 2/2008 |
| KR | 20050032690 A | 4/2005 |
| KR | 20070022975 A | 2/2007 |
| KR | 20100087816 A | 8/2010 |
| KR | 20130085501 A | 7/2013 |
| KR | 20140029984 A | 3/2014 |

* cited by examiner

METHOD FOR BUILDING CLOUD-BASED MEDICAL IMAGE DATABASE FOR PROTECTION OF PATIENT INFORMATION AND READING MEDICAL IMAGE THEREFROM

TECHNICAL FIELD

The present disclosure relates to a method of building a cloud-based medical image database for protecting patient information and reading a medical image therefrom, and more particularly, to a method of building a cloud-based medical image database for protecting patient information and reading a medical image therefrom, which may protect patient's personal information and determine the cause and progress of a disease by extracting patient information data inserted into the medical image when storing, in the cloud-based medical image database, the medical image acquired for diagnosing or treating a patient, encrypting the patient information data by using a block chain encryption technique to transmit and store the same, and decrypting the patient information data by using a block chain decryption technique.

BACKGROUND ART

Nowadays, medical organizations build medical information systems and computerize all processes and records including reception, examinations, prescriptions, treatment, hospitalization, hospital departures, inspection results, etc. for patients by using digital technology. Specifically, a picture archiving and communications system (PACS), which is a medical image processing system, transmitting an image captured by X-ray, CT, or MRI, and a hospital information system (HIS), which is a hospital information system integrating all of these, belong to a medical information system.

However, although the building of medical information systems is an advantage in public health improvement, it involves much risk in terms of personal information protection.

This is because medical information including patient information data not only includes specialized information having a public interest related to the physical body of an individual patient, but also information needing special protection among personal information. Since this digital patient information data is easy to duplicate, in the case where personal information leaks out or inaccurate information is produced, there is a possibility that people's personal privacy may be infringed upon. Therefore, there is a need for effective technology which may protect personal information such as patient information data and prevent infringement of people's privacy.

As technology of the related art for improving the above technology, a method of sharing medical information and a system for sharing medical information are known from U.S. Patent Publication No. 2002/0035485.

U.S. Patent Publication No. 2002/0035485, which is a known technology, is technology providing a method of sharing medical information, the method including: registering unique physical feature information of a patient, for example, fingerprints, a voice, an iris of an eye, and an eye fundus image together with medical information of the patient in a database connected to a server, the server being a medical data providing source; allowing a terminal requesting medical data to request a server, the server being a medical data information source, to transmit medical information of a patient through a communication network; transmitting physical feature information read from a patient; comparing the physical feature information transmitted from the terminal with physical feature information stored in the database; and when the physical feature information from the terminal and the physical feature information stored in the database coincide with each other according to a result of the comparison, transmitting the medical information of the patient stored in the database from the server to the terminal through the communication network.

However, in the case of receiving required patient information data, the known technology provides not only treatment progress data of a patient but also pure personal information such as a name, gender, address, phone number, resident registration number, insurance number, birthday, etc. of an individual patient. In this case, although a medical service is not a service for identifying an individual patient, patient's personal information is exposed.

Also, as another technology of a related art for resolving the above problem, a medical information system and a method for providing medical information, for protecting personal information and supporting medical studies, are known from Korean Publication No. 10-2005-0032690.

The medical information providing system of the known technology according to the other related art discriminates a patient's personal identification information from non-personal identification information, and provides the patient's medical information through a communication network. The medical information providing system includes: a personal identification information database stored in a patient terminal held by a patient and storing the patient's personal identification data; a non-personal identification information database stored in the patient terminal and storing the patient's non-personal identification information; a treatment code generator issuing a treatment code for treatment of the patient at a hospital; a treatment information database storing the patient's treatment data at the hospital; a study information database storing data studied by using the treatment code and the treatment data together with the patient's non-personal identification information; and a treatment code list database stored in the patient terminal and the hospital and storing the issued treatment code. The medical information providing system may prevent the patient's personal information from leaking out by allowing non-personal identification information separated from the patient's personal identification information to be provided together with the treatment code when the patient's medical information is used for medical studies.

However, the known technology according to the other related art protects patient's personal information by simply separating patient information data, and separately managing the non-personal identification information separated from the patient's personal identification information, and the treatment code, when using the patient information data for a medical purpose. Therefore, the known technology according to the other related art is different from technology which allows patient information data acquired through a medical apparatus not to be duplicated, and also guarantees irreversibility such that personal information is not modulated.

As technology for preventing duplication and modulation, block chain encryption technology recently applied to bitcoin, which is an on-line virtual currency, is widely used. There is also a need for technology which may maintain security of patient information data, block hacking, and transparently record data through the block chain encryption technology.

DESCRIPTION OF EMBODIMENTS

Technical Problem

The present disclosure aims to protect patient's personal information by extracting patient information data inserted into a medical image, encrypting the patient's personal information by using a block chain encryption technique to transmit and store the same, and decrypting the patient's personal information by using a block chain decryption technique.

Solution to Problem

According to an aspect of the present disclosure, a method of building cloud-based medical image database for protecting patient information and reading medical image therefrom, includes: acquiring a patient's medical image by using a medical apparatus; separating medical information data and patient information data from the medical image; encrypting the patient information data by using a block chain technique; separately transmitting the encrypted patient information data and the medical information data to a cloud-based medical image database, and storing the same in the cloud-based medical image database; decrypting the encrypted patient information data stored in the cloud-based medical image database by using the block chain technique; and performing diagnosis and consulting by reading the medical information data and the patient information data of the medical image according to a big data processing algorithm.

Advantageous Effects of Disclosure

Therefore, according to a method of building a cloud-based medical image database for protecting patient information, patient information data acquired by a medical apparatus cannot be duplicated, and irreversibility is guaranteed such that personal information cannot be modulated.

MODE OF DISCLOSURE

Figure 1:
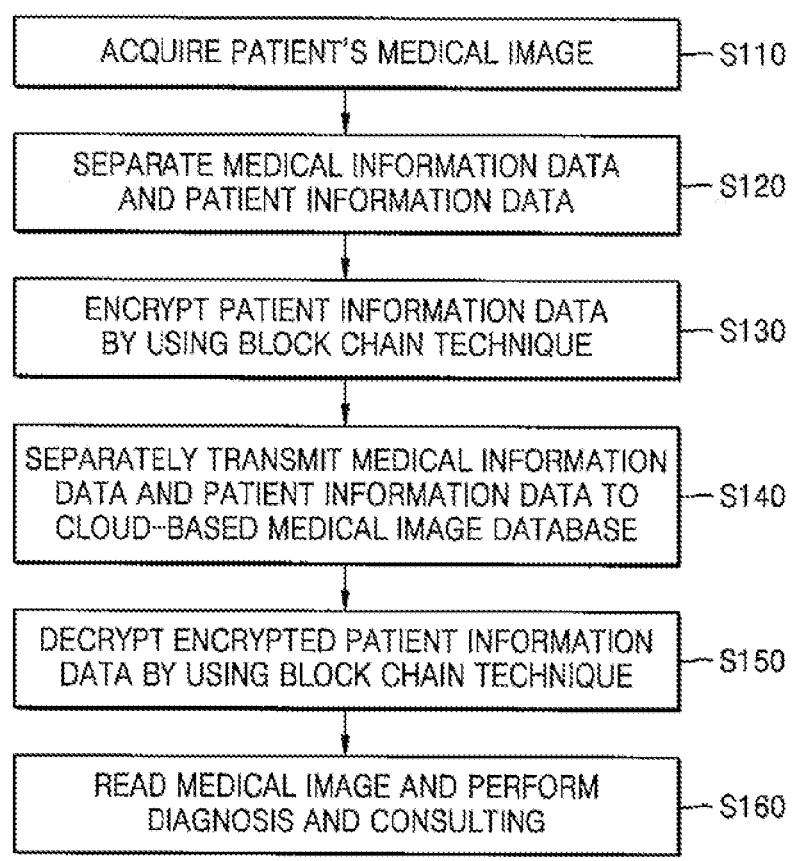
FIG. 1 is a flowchart of a method of building a cloud-based medical image database for protecting patient information and reading a medical image therefrom, according to an embodiment.

Terms and words used for the present specification and claims should not be limited to general or dictionary meanings, and should be construed as meanings and concepts matching a technical spirit of the present disclosure based on a principle that the inventor may properly define concepts of terms to explain his or her disclosure in a best method.

Therefore, since embodiments described in the present specification and a configuration illustrated in the drawings are only most preferred embodiments and do not represent all technical spirits of the present disclosure, it should be understood that various equivalents and modifications which may replace the embodiments may exist at the time of filing of the present application.

Hereinafter, a preferred embodiment of the present disclosure is described in detail with reference to the accompanying drawings.

FIG. 1 is a flowchart of a method of building a cloud-based medical image database for protecting patient information and reading a medical image therefrom according to an embodiment.

As illustrated, a method of building a cloud-based medical image database for protecting patient information and reading a medical image therefrom, includes: acquiring a patient's medical image by using a medical apparatus (S110); separating medical information data and patient information data from the medical image (S120); encrypting the patient information data by using a block chain technique (S130); separately transmitting the encrypted patient information data and medical information data to a cloud-based medical image database and storing the same (S140); requesting the encrypted patient information data stored in the cloud-based medical image database, and decrypting the same by using the block chain technique (S150); and performing diagnosis and consulting by reading the medical image including the medical information data and the patient information data according to a big data processing algorithm (S160).

The method is described below in detail.

In operation S110 of acquiring a medical image of a patient by using a medical apparatus, the medical apparatus collectively denotes medical apparatuses such as medical cameras, medical scanners, X-rays, computerized tomography (CT), magnetic resonance imaging (MRI), ultrasonic capturing apparatuses, and microscopes for clinical inspection which may acquire a medical image of a patient through a medical apparatus.

Also, the medical image acquired by the medical apparatus includes an image in which pure medical information data is combined with patient information data.

In this case, the patient information data of the medical image includes not only a name, address, and resident registration number of the patient, and unique personal information of the patient inserted to the medical image, but also at least one of bio-feature information required for identifying the patient. Also, the medical image may further include at least one of a reading history, a generation history, a treatment record, an access record of the medical image, and location information of an area where the medical image has been generated. The patient information data of the medical image may be automatically inserted when the medical image is generated, or may be arbitrarily added and inserted when the medical image is generated.

After that, operation S120 is performed, operation S120 separating medical information data including only pure medical information, and the patient information data from the medical image, and storing the same.

The medical image is generally stored as a digital data file, and pure medical information data may be discriminated and separated from patient information data, and stored by using a file processing technique for digital data of the medical image.

However, in the case where the medical image is film data, for separation of the pure medical information data from the patient information data, the patient information data is separated and acquired by using text conversion technology which utilizes an OCR algorithm and a pattern recognition algorithm.

Operation S130 encrypts only the patient information data of the medical image data stored in operation S120 by using the block chain encrypting technique.

The above-mentioned block chain is a term used for a bitcoin, which is a kind of virtual currencies recently appearing, and the bitcoin denotes technology preventing double payment by using a P2P network. Also, the block chain is also called a 'public transaction book'. This literally means managing with a transaction book open to the public.

The present disclosure uses the term 'block chain' in the sense that a medical personnel stores and manages patient information data in a medical image acquired from the medical apparatus like the concept of a public transaction book of the block chain.

Figure 2:
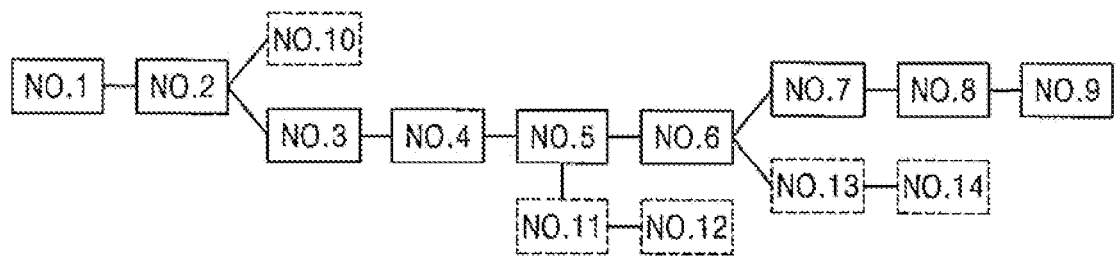
FIG. 2 is a view of an example of a flow of a patient information data block made as a chain configuration by a block chain technique, according to an embodiment.

FIG. 2 is a view of an example of a flow of a patient information data block made as a chain configuration by a block chain technique according to an embodiment.

As illustrated, it may be considered that the patient information data inserted into each medical image is made as a block based on patient information data generated from an initial medical image.

No. 1 of the illustration denotes genesis block data of the patient information data generated from the initial medical image, and patient information data thereon cannot be made without the No. 1 data. Therefore, each patient information data includes information of previous patient information data and such data gather to form an information chain of patient information data. This may be referred to as a patient information data chain for a medical image.

No. 2 to No. 9 of the illustration are interpreted by a hash algorithm corresponding to the block chain decryption, and denote blocks of newly updated patient information data, and patient information data blocks which are parts of an actual patient information data chain. Therefore, the relevant patient information data becomes information security-verified by a relevant network.

Also, patient information data blocks of No. 10 to No. 14 are patient information data blocks which have failed in security verification corresponding to the block chain decryption and thus failed to become a part of the patient information data chain, that is, patient information data blocks which cannot be shared and acknowledged in a network. Therefore, the patient information data may be discarded or cannot be stored and recorded, or cannot be used.

A chain including the No. 1, which is initially created patient information data, and the patient information data, which have won the security verification, is denoted by a 'main chain', and patient information data, which is not classified to the main chain, is denoted by 'orphan/stale/invalid block'. Therefore, only data details included in main chain patient information data are acknowledged as valid.

Figure 3:
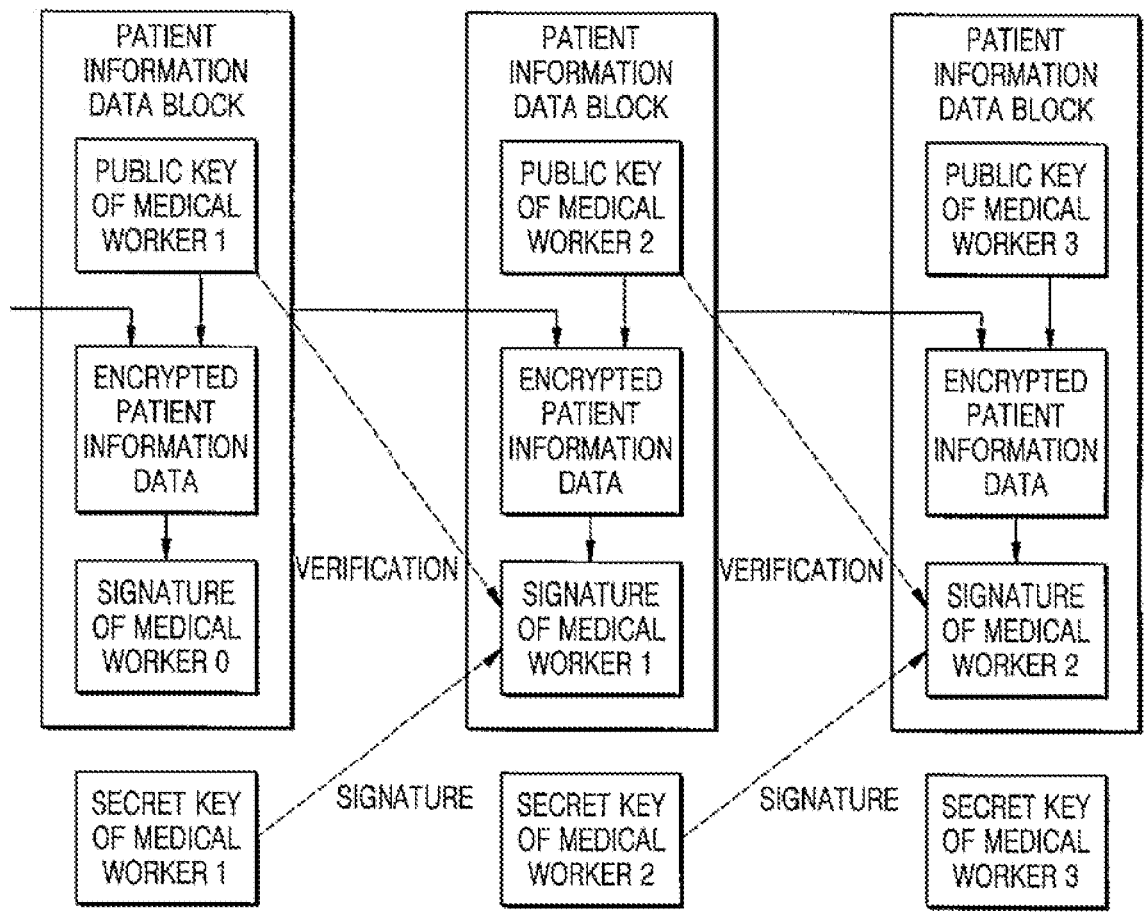
FIG. 3 is a view of an example of an inner structure, verification, and electronic signature of a patient information data block, according to an embodiment.

FIG. 3 is a view of an example of an inner structure, verification, and electronic signature of a patient information data block according to an embodiment.

As illustrated, it is known that the patient information data is hash-encrypted inside the patient information data block, and such encrypted patient information data are connected through a public key and an electronic signature for each medical personnel. Therefore, when previous patient information data is absent, next patient information data cannot be produced. Therefore, respective data are all connected and verify validity of the other data. When data is considered to include discordance details based on existing patient information data details, relevant data is processed as being erroneous.

In other words, the patient information data is defined as a sequence of digital signatures, and respective encryption key owners add a next owner's public key to previous transaction details, and then make a digital signature which encrypts the same with their secret key, and turn over the patient information data.

Therefore, it means that each medical personnel may view the patient information data through verification of a public key and a signature inside the patient information data block in the patient information data chain.

Also, applying the block chain encryption of the patient information data means that a hash algorithm is applied to each element of the patient information data, and the each element of the patient information data is made as a block and processed as a chain through a public key and an electronic signature.

The hash algorithm for the patient information data according to an embodiment uses one of one-direction hash algorithms which receive a message having an arbitrary length and change the message to an output value of a fixed length through a hash algorithm function. For example, for the hash algorithm, one of message digest 4 (MD4), MD5, secure hash algorithm (SHA)-1, SHA-256, and SHA-512 is used.

After that, operation S140 separately transmits the encrypted patient information data and the medical information data to a cloud-based medical image database and stores the same. In this case, the cloud-based medical image database is a storage which is distributed as a peer-to-peer on a network and is accessible by a specific individual or a medical personnel.

Operation S150 decrypts the encrypted patient information data block stored in the cloud-based medical image database by using the block chain technique. This means downloading the encrypted patient information data block stored in the patient information data block chain to decrypt the encrypted patient information data, and processing the same through the block chain decrypting technique by using a personal key and an electronic signature of the medical personnel as illustrated in FIG. 3.

Operation S160 acquires the medical image from the cloud-based medical image database based on the decrypted patient information data, reads medical image data and the patient information data, and performs a diagnosis and consulting by a medical personnel.

In this case, the medical image may be read and diagnosis and consulting may be performed according to a big data processing algorithm based on the medical image and the patient information data.

Therefore, the present disclosure provides a method of building a cloud-based medical image database for protecting patient information and reading a medical image therefrom, which may protect a patient's personal information and determine the cause and progress of a disease, by extracting patient information data inserted to a medical image, encrypting the patient information data by using the block chain encrypting technique to transmit and store the same, and decrypting the patient information data by using the block chain decrypting technique.

While the present disclosure has been particularly shown and described with reference to embodiments thereof, the present disclosure is not limited thereto and it will be understood by those of ordinary skill in the art that various changes in form and details may be made therein without departing from the spirit and scope of the following claims.

The invention claimed is:

1. A method of budding a cloud-based database, using a server, for protecting patient information and reading a medical image therefrom, the method comprising:
   acquiring a first medical image of a patient by using a medical apparatus corresponding to a first medical personnel; and
   generating a first block of a main chain by adding a public key of a second medical personnel assigned to receive and access the first medical image on a first patient information data generated from the first medical image.

2. The method of claim 1, wherein the medical image is an image in which the medical information data is combined with the patient information data, the medical information data being acquired by one of a medical camera, a medical scanner, an X-ray, computerized tomography (CT), magnetic resonance imaging (MRI), an ultrasonic capturing apparatus, and a microscope for clinical inspection.

3. The method of claim 1, wherein the patient information data of the medical image comprises at least one of personal information of the patient or bio-feature information for identifying the patient both being inserted into the medical image, and further comprises at least one of a reading history, a generation history, a treatment record, an access record of the medical image, and location information of an area where the medical image was generated.

4. The method of claim 1, wherein when the medical image is film data, to separate the medical information data and the patient information data, the patient information data is acquired by using text conversion technology which utilizes an OCR algorithm and a pattern recognition algorithm.

5. The method of claim 1, wherein the generating further comprises:
   separating a first medical information data and the first patient information data from the first medical image.

6. The method of claim 1, wherein generating further comprises:
   applying a hash algorithm to the first patient information data; and
   adding the public key of the second medical personnel on the hashed first patient information data and encrypting through a digital signature using a private key of the first medical personnel.

7. The method of claim 1, wherein the generating comprises:
   encrypting the first block through a digital signature using a private key of the first medical personnel.

8. The method of claim 1, wherein further comprises acquiring a second medical image of the patient using a medical device corresponding to the second medical personnel;
   separating a second medical information data and a second patient information data from the second medical image;
   applying a hash algorithm to the second patient information data;
   generating a second block by adding a public key of a third medical personnel on the hashed second patient information data and encrypting through a digital signature using a private key of the second medical personnel.

9. The method of claim 8, wherein further comprises verifying the second block by decrypting the second block encrypted through the digital signature using the public key of the second medical personnel applied to the first block.

10. The method of claim 9, wherein the verifying further comprises:
    if the decryption is successful, determining the second block as a valid block, connecting the second block to the main chain, transmitting and storing the main chain to which the second block is connected and the second medical information data to the cloud-based database, and
    if the decryption fails, determining the second block as an invalid block and discarding the second patient information data.

11. The method of claim 10, wherein the verifying further comprises:
    downloading a block of the main chain from the cloud-based database;
    decrypting the downloaded block using a private key of medical personnel used for encryption of the downloaded block; and
    identifying the medical information data and the patient information data of the medical image corresponding to the decrypted block of the main chain.

12. The method of claim 11, wherein the cloud-based database is a storage which is distributed peer-to-peer on a network and is accessible by a medical personnel.

* * * * *

UNITED STATES PATENT AND TRADEMARK OFFICE
CERTIFICATE OF CORRECTION

PATENT NO. : 11,893,124 B2
APPLICATION NO. : 17/714210
DATED : February 6, 2024
INVENTOR(S) : Minhwa Lee It is certified that error appears in the above-identified patent and that said Letters Patent is hereby corrected as shown below:

In the Claims

Column 7 In Lines 2-12:
1. A method of budding a cloud-based database, using a server, for protecting patient information and reading a medical image therefrom, the method comprising:
    acquiring a first medical image of a patient by using a medical apparatus corresponding to a first medical personnel; and
    generating a first block of a main chain by adding a public key of a second medical personnel assigned to receive and access the first medical image on a first patient information data generated from the first medical image.

Should be corrected to be:
1. A method of building a cloud-based database, using a server, for protecting patient information and reading a medical image therefrom, the method comprising:
    acquiring a first medical image of a patient by using a medical apparatus corresponding to a first medical personnel; and
    generating a first block of a main chain by adding a public key of a second medical personnel assigned to receive and access the first medical image on a first patient information data generated from the first medical image.

Signed and Sealed this
Thirtieth Day of April, 2024

Katherine Kelly Vidal
*Director of the United States Patent and Trademark Office*